US012440361B2

(12) United States Patent
Seifert et al.

(10) Patent No.: US 12,440,361 B2
(45) Date of Patent: Oct. 14, 2025

(54) ORTHOPAEDIC JOINT AND METHOD FOR CONTROLLING SAME

(71) Applicant: OTTO BOCK HEALTHCARE PRODUCTS GMBH, Vienna (AT)

(72) Inventors: Dirk Seifert, Vienna (AT); Florian Fuchs, Hollabrunn (AT)

(73) Assignee: OTTO BOCK HEALTH CARE PRODUCTS GMBH, Vienna (AT)

( * ) Notice: Subject to any disclaimer, the term of this patent is extended or adjusted under 35 U.S.C. 154(b) by 789 days.

(21) Appl. No.: 17/771,121

(22) PCT Filed: Oct. 7, 2020

(86) PCT No.: PCT/EP2020/078102
§ 371 (c)(1),
(2) Date: Apr. 22, 2022

(87) PCT Pub. No.: WO2021/078516
PCT Pub. Date: Apr. 29, 2021

(65) Prior Publication Data

US 2022/0370224 A1 Nov. 24, 2022

(30) Foreign Application Priority Data

Oct. 22, 2019 (DE) ..................... 10 2019 128 508.9

(51) Int. Cl.
*A61F 5/00* (2006.01)
*A61F 5/01* (2006.01)

(52) U.S. Cl.
CPC .......... *A61F 5/0102* (2013.01); *A61F 5/0125* (2013.01); *A61F 2005/0167* (2013.01)

(58) Field of Classification Search
CPC ............................. A61F 5/0102; A61F 5/0125
(Continued)

(56) References Cited

U.S. PATENT DOCUMENTS 7,416,537 B1 * 8/2008 Stark ..................... A61F 5/0125 600/595
2011/0130846 A1 6/2011 Kampas et al.
(Continued)

FOREIGN PATENT DOCUMENTS

DE 10 2008 024 747 A1 12/2009
DE 10 2009 052 887 A1 5/2011
(Continued)

OTHER PUBLICATIONS

DE-102009052887-B4 translation (Year: 2016).*
(Continued)

*Primary Examiner* — Kim M Lewis
(74) *Attorney, Agent, or Firm* — HOLLAND & HART LLP

(57) ABSTRACT

The invention relates to an orthopaedic joint comprising an upper part and a lower part pivotably mounted thereon and a resistance device which is located between the upper part and the lower part and provides resistance against a pivoting movement about a pivot axis, and has a resistance adjusting device coupled to a control device which is coupled to at least one sensor such that the resistance can be adjusted by means of the control device on the basis of sensor data transmitted from the at least one sensor to the control device, a function is stored in the control device in which the joint is locked against pivoting in at least one direction in accordance with the sensor data, the function can be activated for locking and deactivated for unlocking on the basis of the sensor data.

15 Claims, 6 Drawing Sheets

(58) Field of Classification Search
USPC .................................................... 602/16, 26
See application file for complete search history.

(56) References Cited

U.S. PATENT DOCUMENTS

| | | | |
|---|---|---|---|
| 2012/0226364 | A1 | 9/2012 | Kampas et al. |
| 2018/0028390 | A1 | 2/2018 | Dietl et al. |

FOREIGN PATENT DOCUMENTS

| | | | | |
|---|---|---|---|---|
| DE | 102009052887 | B4 * | 9/2016 | ............... A61F 2/64 |
| DE | 10 2016 107 743 | A1 | 10/2017 | |
| DE | 10 2016 114 075 | B3 | 11/2017 | |
| WO | 01/43669 | A1 | 6/2001 | |
| WO | WO-2011057790 | A1 * | 5/2011 | ............... A61F 2/64 |
| WO | 2016/169853 | A1 | 10/2016 | |

OTHER PUBLICATIONS

WO-2011057790-A1 translation (Year: 2011).*
"International Search Report and Written Opinion of the International Searching Authority," issued in connection with Int'l Appl. No. PCT/EP2020/078102, published Apr. 29, 2021 (15 pages).

* cited by examiner

ORTHOPAEDIC JOINT AND METHOD FOR CONTROLLING SAME

The invention relates to an orthopedic joint, in particular a prosthetic joint or orthotic joint, comprising an upper part and a lower part pivotably arranged on the latter, and a resistance device which is arranged between the upper part and the lower part and provides resistance against a pivoting movement of the upper part relative to the lower part about a pivot axis, and which has an adjustment device by means of which the resistance is adjustable, wherein the adjustment device is coupled to a control device, which is coupled to at least one sensor, such that the resistance is adjustable by means of the control device on the basis of sensor data that are transmitted from the at least one sensor to the control device, wherein the control device has stored in it a function in which the joint is locked against pivoting in at least one direction in accordance with the sensor data, and the function can be activated for locking and deactivated for unlocking on the basis of the sensor data. The invention likewise relates to a method for controlling an orthopedic joint, in particular a prosthetic joint or orthotic joint, comprising an upper part and a lower part pivotably arranged on the latter, and a resistance device which is arranged between the upper part and the lower part and provides resistance against a pivoting movement of the upper part relative to the lower part about a pivot axis and has an adjustment device by means of which the resistance is adjusted on the basis of sensor data transmitted from at least one sensor to a control device connected to the adjustment device, in such a way that the joint is locked against pivoting upon activation of a function and the joint is unlocked upon deactivation of the function.

Orthopedic aids such as prostheses, orthoses or also exoskeletons have joints for connecting two components of the orthopedic aids to each other movably. A pivotability of the two components relative to each other about a pivot axis, which can be designed as a fixed pivot axis in a single-axis joint or as a migrating pivot axis in a multi-link system, makes it possible, for example, to guide and support a movement by an orthosis or to perform movements that correspond to the natural movement. In the case of a prosthesis or orthosis of the lower extremity, a movement pattern can thus be obtained that approximates to the natural movement behavior. A prosthetic foot is connected to a lower-leg socket or a lower-leg tube via an ankle joint. The lower-leg tube is fastened to a prosthetic knee joint, which is arranged on a thigh stump via a thigh socket. The same applies to orthoses, which are placed on existing limbs. The orthopedic aid can bridge one or more joints, for example a knee joint and/or an ankle joint or, in the case of use on an upper extremity, an elbow joint and/or a wrist.

To be able to influence the pivoting about the pivot axis, dampers are known from the prior art which provide resistance to an extension movement and/or flexion movement. The resistance can be adjustable. It is likewise possible that the resistance changes depending on load situations or movement parameters. In the case of a rapid movement, for example, a greater resistance can automatically be made available. It is likewise possible to set or change a resistance curve depending on an angle or depending on a load. The setting can be done mechanically or by mechatronics. In a mechatronic configuration of the damper or of the resistance device, movement data, load data and/or also position data are captured via sensors and transmitted to a control device. In the latter, an activation signal or deactivation signal for an actuator or for an adjustment device is generated from said data in order to reduce or increase the respective resistance. This can be done, for example, by changing a cross section of flow in a hydraulic damper or by changing a magnetic field in the case of magnetorheological resistance devices. The resistance device can also be configured as an electric motor which, in generator mode, provides resistance against a pivoting movement.

Particularly in the case of computer-controlled joints or joint devices with sensors, different control programs can be stored in order to be able to provide an adapted resistance behavior for different loads or movement situations. For walking on a level surface, a resistance profile for a step cycle can be generated that differs from walking on a slope. Furthermore, in computer-controlled joints, functions for special situations are stored in which, for example, a joint is locked by repeated execution of a defined movement pattern or locking is activated or deactivated after a defined period of time. The "C-Legg" from Ottobock has a stance function that can be activated via a movement pattern. Furthermore, there is the choice of an intuitive stance function that blocks the joint when it is held still in a flexed position. When the position of the leg changes, the stance function is deactivated.

The parameters for the activation and deactivation of special functions are either fixed or are determined individually for the patient and set once.

The object of the present invention is to make available a joint and a method for controlling a joint that is more easily adaptable to the needs of the respective user.

This object is achieved by a joint having the features of the main claim and by a method having the features of the additional independent claim. Advantageous embodiments and developments of the invention are disclosed in the subclaims, the description and the figures.

The orthopedic joint comprising an upper part and a lower part pivotably arranged on the latter, and a resistance device which is arranged between the upper part and the lower part and provides resistance against a pivoting movement of the upper part relative to the lower part about a pivot axis, and which has an adjustment device by means of which the resistance is adjustable, wherein the adjustment device is coupled to a control device, which is coupled to at least one sensor, such that the resistance is adjustable by means of the control device on the basis of sensor data that are transmitted from the at least one sensor to the control device, wherein the control device has stored in it a function in which the joint is locked against pivoting in at least one direction in accordance with the sensor data, and wherein the function can be activated for locking and deactivated for unlocking on the basis of the sensor data, provision being made that at least one parameter for activating the function and at least one parameter for deactivating the function are correlated with one another. With such a joint, it is possible to set the characteristics for activation and deactivation of the lock. The behavior of the patient for triggering locking or for canceling locking can be correlated using several parameters. The parameters or the parameter leading to the locking of the joint can be modified, for example, with regard to the sensitivity and can lead particularly quickly to locking of the joint; at the same time, the parameter leading to the deactivation of the joint is also modified. The respective parameter can be composed of several sensor values or properties, for example a time factor and a movement factor. If, for example, the joint is not moved for a certain time, this can serve as a parameter for the fact that a joint is to be locked. A less sensitive parameterization provides that locking takes place only after the user has been completely still for quite a long period of time. A more sensitive parameterization can provide that small relative movements or pivoting are allowed in the same time period or that locking is already activated or initiated when the joint is completely still and has been still for a short duration or when the joint is briefly and almost completely immobilized. Conversely, the corresponding deactivation can likewise be set to be sensitive, for example by the lowering of a threshold value for the change of spatial position or by a slight change in an axial load.

A joint can be locked by being blocked in a form-fitting manner against a relative movement of upper part and lower part. It is likewise possible that the resistance device, for example a hydraulic damper, a brake, a magnetorheological damper, a linear hydraulic system and/or an electric motor is set, in generator mode, to such a high resistance value that a displacement is not to be expected under normal loading or else a movement of upper part and lower part relative to each other is only possible very slowly or with application of very high forces and moments. Locking can thus include complete immobilization of the joint or a very high resistance against flexion and/or extension.

The duration of a static state of the joint device can be stored as a parameter for activating the function. From a defined threshold value of the static state, the control device assumes that the joint should be locked and causes the adjustment device to increase the resistance against flexion and/or extension by the resistance device. To do this, valves can be closed, magnetic fields can be applied or switched off, or mechanical resistances such as brakes or form-fit elements can be activated or engaged. In addition to the time and the presence of a static state, further sensor values or states can also be incorporated into the parameter, for example loads, changes in loads, angular positions of joint components relative to one another, or absolute positions of joint components in space.

A movement of the lower part, a movement of the upper part and/or a loading of the joint or a joint component and/or rates of change in the movement and/or the load can be stored as parameters for activating or deactivating the function. In addition, further parameters or variables can be stored by which it is possible to activate or deactivate the locking by the resistance device. For example, a sensor can be used to detect a very high acceleration in a direction that would not occur in a normal movement sequence. If, for example, a joint is moved back and forth several times in opposite directions, these accelerations and changes in the direction of movement can be used as a basis for the locking or for increasing the resistance to a specified value.

A spatial position of the upper part, a spatial position of the lower part and/or a spatial position of a connecting line between two points located proximally and distally of the pivot axis can be used as parameters for deactivating the function. The connecting line between two fixed points can be defined in advance as what is called a joint chord. The spatial position of the joint chord allows conclusions to be drawn concerning the movement situation. For example, the spatial position of a leg chord between a thigh and a lower leg, for example between the hip joint and the ankle joint, can be used to determine whether a user or patient is standing, lying down or seated. If a knee joint is locked in an extended, standing position, a forward inclination or rearward inclination of the upper part together with the lower part, for example when sitting down, can cause the joint device to be unlocked by loosening of the resistance device or reduction of the flexion resistance.

In a further development of the invention, provision is made that threshold values for the parameters for activation and/or deactivation are stored. The threshold values can be stored in a memory, which is coupled to the control device or is integrated therein. The threshold values can be variable, such that the user or an orthopedic technician has the possibility of carrying out an individual adjustment to the respective user. The threshold values can be adjusted steplessly or in steps. A stepless adjustment can be useful, for example, in the case of a time parameter or a time variable. A step-by-step adjustment makes it easier to feel the different threshold values and simplifies setting. Particularly in the case where several measured values are combined into one parameter, setting can be made easier by combination of the values and by a specified gradation. For example, a sensitivity of the locking in several stages from stable through normal to sensitive can be facilitated by a selection of symbols or icons. A stepless adjustment can take place via touch-sensitive setting elements on an output device or via rotary knobs or slide controls, which can also be digitized and displayed virtually.

The threshold values for the activation and deactivation can be positively correlated. Accordingly, with a sensitive setting for the activation of a lock, a minor action or a low-threshold impulse is required in order to carry out the deactivation. For example, if a joint is locked after a short time with a partial immobilization, a positive correlation with the deactivation means that a slight displacement or a slight relief or loading or acceleration is sufficient to cancel the locking again and allow flexion and/or extension.

The control device can be connected to a display and to an operating element for changing the parameters and/or the threshold values of the parameters, so that it is easy for a user or an orthopedic technician to carry out an adaptation to the respective user. A higher-order criterion such as "sensitivity", as a so-called master controller, can enable a simple change. In addition, it is possible that the individual values or influencing variables for the parameters such as time, load, displacement, extent of the displacement, speeds, accelerations, moments or positions in space can be individually adapted and individually combined with one another.

To make available the necessary sensor values, a gyroscope, an inertial measuring unit, an angle sensor, a force sensor and/or a time sensor can be coupled to the control device, so as to be able to make available the necessary sensor data to the control device. Several of these sensors can also be assigned to the orthopedic joint or to the orthopedic aid and can in particular be connected to the joint or to the orthopedic aid. In addition to directly attaching the sensors or the sensor to the joint or to further components that are attached to the joint, it is also possible to attach the sensors to the user, separately from the orthopedic aid, and to transmit the sensor data by cable or wirelessly to the control device. The control device accommodates the necessary components for the electronic processing of the sensor data, in particular at least one processor, at least one memory, a power supply, storage elements for the required software, and a device for capturing sensor data and outputting control data with which the adjustment device for the resistance device can be activated or deactivated.

In the method for controlling an orthopedic joint comprising an upper part and a lower part pivotably arranged on the latter, and a resistance device which is arranged between the upper part and the lower part and provides resistance against a pivoting movement of the upper part relative to the lower part about a pivot axis, and which has an adjustment device, by means of which the resistance is adjusted on the basis of sensor data transmitted from at least one sensor to a control device connected to the adjustment device, in such a way that the joint is locked against pivoting upon activation of a function and unlocked upon deactivation of the function, provision is made that at least one threshold value for a parameter for activating the function and at least one threshold value for a parameter for deactivating the function are correlated with one another. The threshold values for deactivation and activation are stored in the control device and are compared with the sensor data. The sensor data can either be transmitted already processed by the sensors or can be processed as so-called raw data in the control device and compared in processed form with the threshold values stored in the software. If a parameter or a threshold value for a parameter for activation is changed, this leads to a change in the parameter for deactivation and, if applicable, vice versa. In the software in the control device, a threshold value is implemented for the orthopedic technician and/or the user, which threshold value permits adjustability or a selection via the stability or via the response behavior of the control and thus the response behavior of the lock. The setting value can change several parameters of the function, for example a stance function, at the same time and in a well-coordinated manner. For example, if a fine or sensitive response behavior is desired in order to activate the function, the function is parameterized in such a way that, for example, a short rest position is sufficient to provide locking against flexion and/or extension. At the same time, the necessary threshold values for canceling the lock, i.e. for deactivating the lock and thus enabling or reducing the locking resistance, are lowered if a positive correlation is present. The threshold values are, for example, a range of motion or an angular speed of a joint segment. In the case of a negative correlation, the threshold values for canceling the lock are increased. Conversely, with a desired high degree of stability and a desired locking only in clear cases, the function can be parameterized in such a way that a longer rest position or a longer period of time of a static state is necessary to achieve locking. In the case of a positive correlation of the deactivation parameters, a greater range of motion, a greater angular speed or a higher acceleration is necessary in order to cancel the locking or lower the resistance to an appropriate level.

If the threshold values or the parameters for activation and deactivation are positively correlated with one another, this is generally advantageous for a user, since, for example, uncertain patients prefer unambiguous locking and unlocking situations, while users of joints who prefer sensitive locking generally also prefer a sensitive control for unlocking.

The function can be activated in particular on the basis of the duration of a static state of the joint device, in particular on the basis of the duration of a static state in a specific orientation of a component or in a specific orientation of a joint chord.

The function can be deactivated on the basis of a movement, i.e. canceling of the static state, of the lower part, the upper part, or a load on the joint or a joint component, while on the other hand a loading of the joint can also be a criterion for activating a lock. The locking can also be canceled by the detection of speeds or accelerations or by using special orientations of joint components in space or with respect to one another.

In particular, a function that causes locking can be deactivated on the basis of a spatial position of the upper part, a spatial position of the lower part and/or a connecting line between two points located proximally and distally of the pivot axis.

The threshold values for the parameters for activation and/or deactivation are preferably variable, in particular adjustable in steps or steplessly. The parameters can be shown on a touch-sensitive display, for example, such that, by adjusting a displayed slide or rotary knob or, in the case of a step-by-step setting, by touching an icon, a corresponding parameter adjustment or threshold value adjustment of the respective parameter is carried out. The user or orthopedic technician can be informed about the threshold values and the properties of the latter via one or more icons on the display, so that the person in question receives the necessary information as to which settings have which effects.

Embodiments of the invention are explained in more detail below with reference to the accompanying figures, in which.

Figure 1:
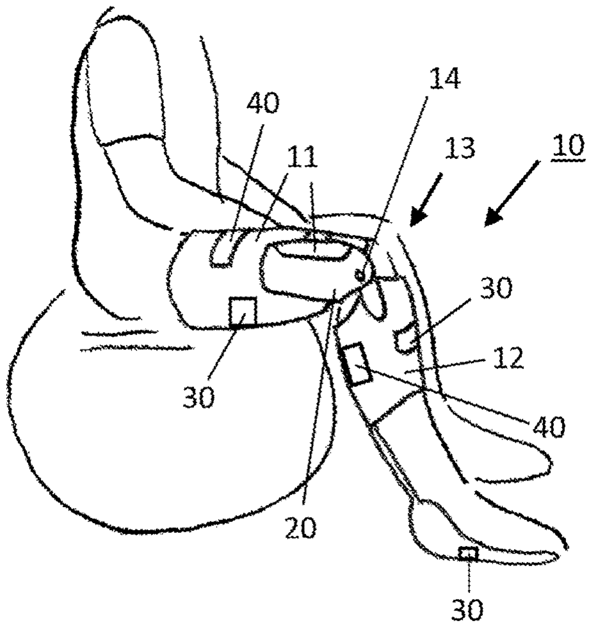
FIG. 1 shows an orthopedic aid in the form of an orthosis in a first position.

FIG. 1 shows a schematic representation of an orthopedic aid in the form of an orthosis 10 comprising an upper part 11, which is connected to a lower part 12 via a joint 13. The lower part 12 is connected to the upper part 11 about a pivot axis 14. The upper part 11 of the leg orthosis is designed as a shell or rail for receiving a thigh, and the lower part 12 is designed to bear on a lower leg and has a foot part which is integrally formed on the lower part 12 or alternatively fastened thereto. Arranged on the upper part 11 is a resistance device 20, by means of which a resistance against pivoting of the lower part 12 relative to the upper part 11 can be adjusted. The resistance device 20 can in particular be used to block a pivoting movement and is designed, for example, as a hydraulic damper, a brake, a magnetorheological resistance device or the like. Sensors 30 are arranged on both the upper part 11 and the lower part 12 and can capture information concerning the current spatial position, the position of the respective components relative to one another and, optionally, loads, angular positions and/or accelerations of said respective components. The sensors 30 are coupled to a control device 40, either by cable or wirelessly. Within the control device 40, the sensor data are evaluated and compared with threshold values that are stored in programs or memories within the control device 40. If the corresponding criteria for locking or unlocking the joint 13 are met, the control device 40 outputs a control command to an adjustment device 60, which is arranged on the resistance device 20. The adjustment device, for example a motor or actuator for adjusting a valve, a coil for changing a magnetic field, or another actuating device or another influencing element, then acts within the resistance device 20 or on the resistance device 20 and locks or unlocks the joint 13.

Figure 2:
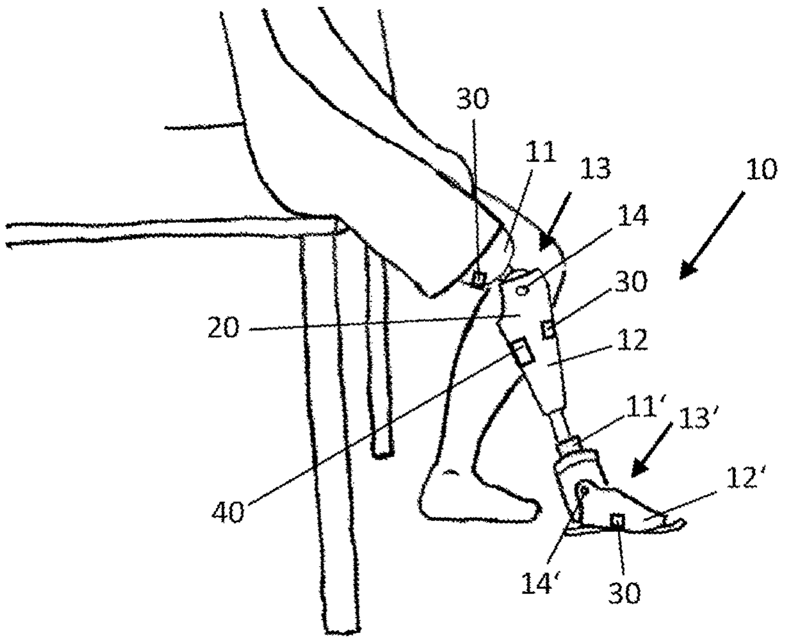
FIG. 2 shows an orthopedic aid in the form of a prosthesis in a first position.

FIG. 2 shows a corresponding orthopedic aid in the form of a prosthesis. Instead of a thigh shell, the upper part 11 is designed as a thigh socket for receiving a thigh stump, the joint 13 is designed as a prosthetic knee joint, and the lower part 12 as a lower-leg tube or lower-leg part. At the distal end of the lower-leg part 12, a prosthetic foot is pivotably arranged on a joint 13' in the form of a prosthetic ankle joint. The pivoting takes place about a pivot axis 14', such that the lower-leg part 12 is to be seen as a lower part in relation to the prosthetic knee joint 13 and as an upper part 11' in relation to the prosthetic ankle joint 13'. The foot part is then the lower part 12'. There are also sensors 30 arranged on the prosthesis: on the thigh socket as upper part 11, for example, at least one gyroscope, an acceleration sensor and/or angle sensor; on the lower-leg part as lower part 12, for example, a spatial position sensor or an IMU, an axial force sensor or the like; on the foot part, for example, a moment sensor and/or force sensor. Multiple sensors can be arranged on the respective component or can be assigned thereto. In addition, a time sensor or a timing element is arranged or formed in the control device 40 and determines a change of state or the duration of a detected state. In the embodiments of FIGS. 1 and 2, the user of the orthopedic aid 10 is in a seated position in which the knee joint is bent. The bent position is determined, for example, via an angle sensor which detects the angular position of the upper part 11 and lower part 12 in space or with respect to each other. In addition, the foot part or the prosthetic foot is relieved since, on account of the seated position, part of the body weight is not introduced into the orthopedic aid 10. This low axial load is detected, for example, by a force sensor in the foot part or the prosthetic foot. It may be convenient for the user if a joint 13, 13', that is to say the orthotic or prosthetic knee joint or the prosthetic ankle joint, is locked when the user is in such a position for a certain period of time. Using predetermined parameters such as axial loading, angular position and/or duration of a static state, a function can be activated with which the respective joint 13, 13' is locked. To unlock the joint 13, 13', it is accordingly necessary to detect a change in situation. The sensor values and parameters for deactivating the lock, i.e. for unlocking the respective joint 13, 13', are likewise specified, for example an increase in the axial loading in the foot part or the prosthetic foot, a change in the spatial position of the upper part 11 or a moment about a pivot axis 14, 14'. If the predetermined threshold values are reached here, the control device 40 outputs a corresponding signal and the resistance device 20 is unlocked by the adjustment device 60.

Figure 3:
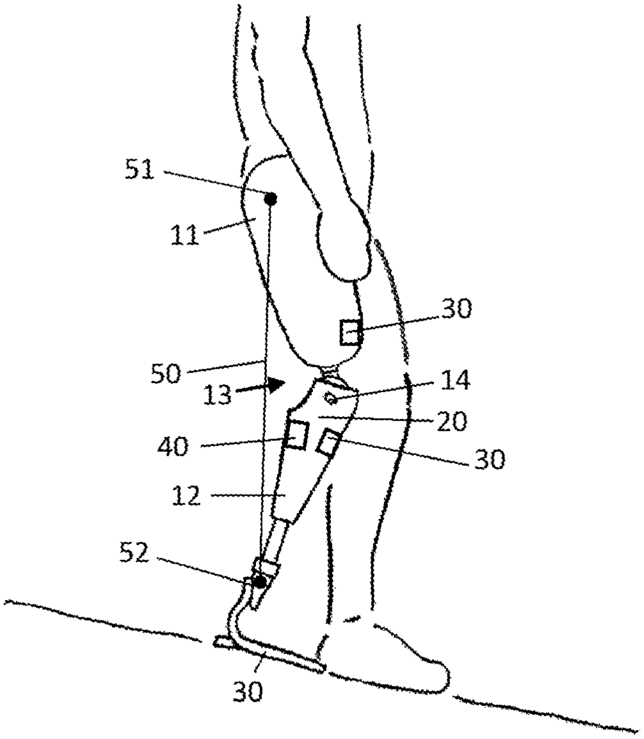
FIGS. 3 to 6 show a prosthesis according to FIG. 2 in different positions.

FIGS. 3 to 6 show different situations of use of the orthopedic aid 10, taking the example of a prosthetic leg with a thigh socket, a prosthetic knee joint, a lower-leg part and a jointless prosthetic foot. In FIG. 3, a user is standing on an inclined plane, in FIG. 4 the user is leaning against a wall, in FIG. 5 the user is bent forward and leaning on a table, and in FIG. 6 the user is seated on a raised chair. The basic set-up of the prosthesis according to FIGS. 3 to 6 corresponds to that of the prosthesis according to FIG. 2, the difference lying in the design of the orthotic foot as a jointless foot, that is to say without second joint 13' and pivot axis 14'. To make matters clearer, the figures do not include all of the components.

Figure 4:
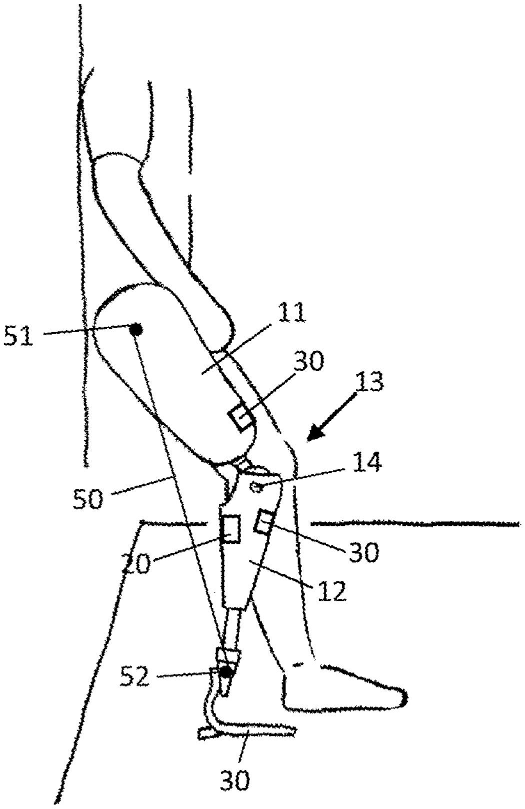
Figure 5:
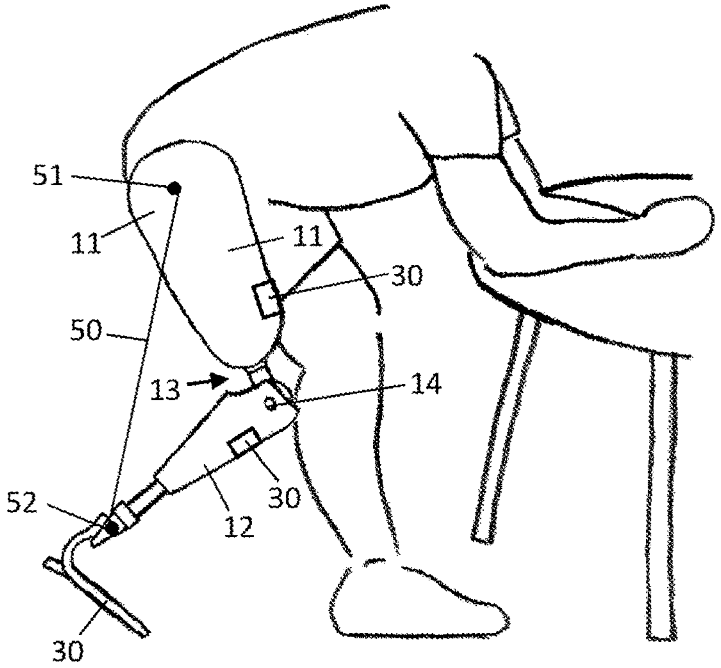
Figure 6:
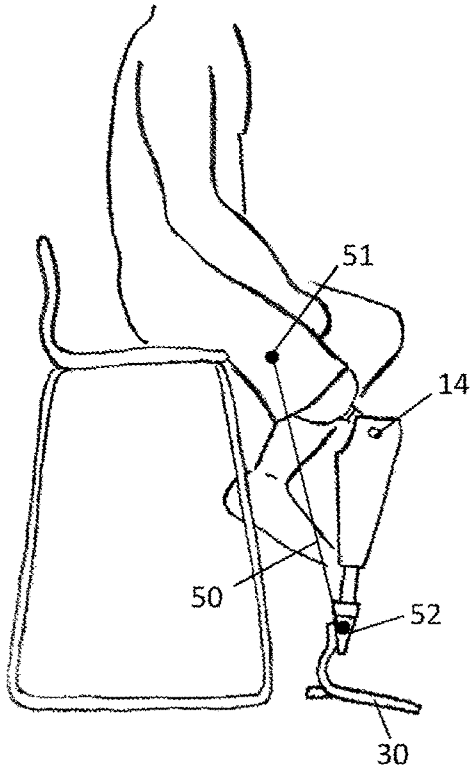

A connecting line 50 between two points 51, 52 on the prosthesis is indicated in FIGS. 3 to 6. The proximal point 51 is positioned in the region of the greater trochanter, while the distal point 52 is positioned in the region of the natural ankle joint at the distal end of the lower-leg part 12. The connecting line 50 represents what is called the leg chord, the orientation and the length of which allow conclusions to be drawn concerning the absolute position of the leg and of the respective components and the movement situation. The spatial position of the connecting line 50 or leg chord can be calculated on the basis of the spatial position of the upper part 11 and/or the lower part 12 and also the known distances of the points 51, 52 to the pivot axis 14, and the angular setting between upper part 11 and lower part 12. In FIG. 3, the leg chord 50 is tilted slightly forward in the direction of walking and, on account of to the slight flexion in the knee joint 13, has an almost maximum length. The flexion in the knee joint in FIG. 4 is greater than in FIG. 3, but the leg chord 50 is inclined rearward. The leg chord 50 in the position according to FIG. 5 is quite strongly inclined forward and shortened compared to the position according to FIG. 3. The spatial inclination of the seated position according to FIG. 6 corresponds approximately to the inclination of the leg chord 50 according to FIG. 4, but the leg chord 50 is much shorter on account of the greater knee flexion. In addition, different axial forces are detectable in all positions, for example via a force sensor 30 in the foot part, and the moments about the knee joint axis 14 are likewise different in each situation of use.

For example, in order to be able to adapt the time at which the prosthetic knee joint 13 is locked in the respective situation to the wishes or needs of the respective user, the control device 40 is assigned an operating element, which can be arranged directly on the prosthesis. Alternatively, the operating element can be in wireless communication with the control device 40 and, for example, be an application on a cell phone, a remote control, a computer or the like. The operating element can also be designed as a rotary knob, slide control or other setting device.

If, for example, the user is in a position according to FIG. 4, this may mean that the user would like to rest. For this purpose, it is helpful if the joint 13 is locked. It may be desirable for this locking to be carried out very quickly by the resistance device 20, in order to reduce the effort on the part of the user. If the user changes his position, the prosthesis should restore its normal properties and its mobility as quickly as possible, for example for walking on level ground. Accordingly, a short period of time is set for the locking after detection of the position according to FIG. 4, for example by detection of the rearward inclination of the leg chord 50 with a torque about the pivot axis 14 and an otherwise static position of the prosthesis. To unlock the resistance device 20, only a slight change in the spatial position of the leg chord 50 is then required, for example a slight tilting forward.

If the user is in a bent forward position according to FIG. 5, for example when working at a low table, rapid locking of the knee joint 13 may be desired, but rapid unlocking, and with it a risk of instability, may be undesirable. For such a position of the leg chord 50 with a corresponding load situation, negative feedback may be advantageous, i.e. rapid locking in the event of slow or sluggish unlocking.

Figure 7:
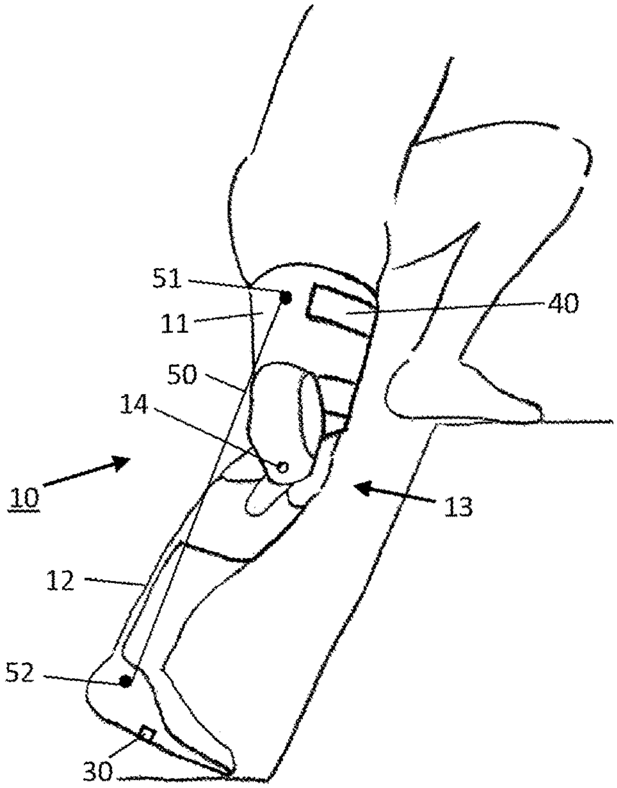
FIG. 7 shows an orthosis according to FIG. 1 during use.

In FIG. 7, the orthopedic aid 10 is shown as an orthosis; in this position too, rapid locking of the orthotic knee joint 13 in a static position, for example when the user is working in this position, may be useful. In addition to the orientation of the leg chord 50, its static state over a certain period of time can serve as an indication that locking should take place. In addition, axial loads or moments can be detected via sensors 30 in the foot part, so that rapid locking may be desirable in the event of high loading of the leg with the orthosis. If the load situation and the situation of use change, rapid unlocking may be required. For this purpose, a control panel, a display or an operating element can be arranged on the control device 40, which is located on the thigh part or upper part 11 of the orthosis, so that the user can easily adjust the sensitivity during use.

Figure 8:
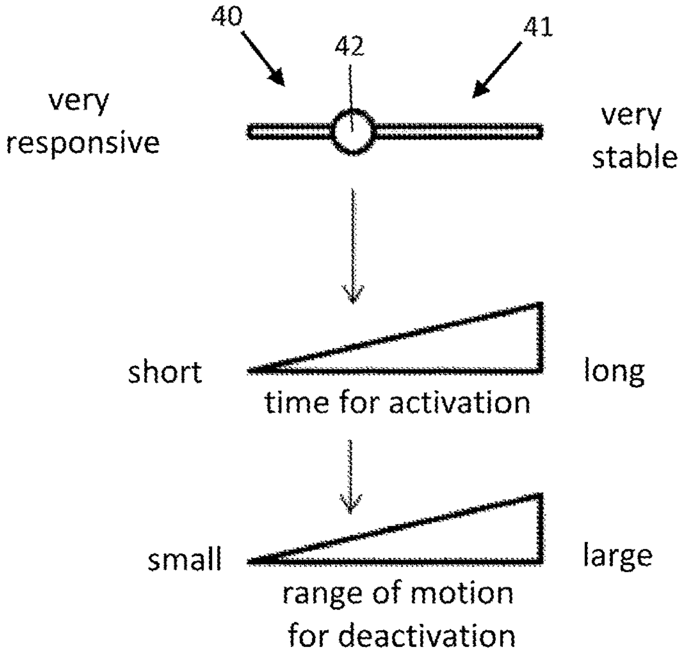
FIG. 8 shows a schematic representation of the adjustment of locking and unlocking.

FIG. 8 shows, by way of example, part of a control device 40 with an operating element 42, which is designed as a touch-sensitive element in a display device 41, for example a display screen. The operating element 42 can also be designed as a mechanical operating element, for example as a knob, slide or switch. The position of the operating element 42 can be shifted between the two end values for very sensitive (very responsive), with rapid locking and correspondingly rapid unlocking, and very stable. The adjustment can take place steplessly or in steps. Below the operating element 42, the figure shows how the time for the activation of the lock by the resistance device 20 changes, namely from short to long. For deactivating the lock, the parameter associated with this in the exemplary embodiment is shown underneath, namely the range of motion, for example the pivoting of a component or the pivoting of the leg chord 50. In the exemplary embodiment shown, there is a positive correlation between the parameter for the activation (duration of a static state) and the parameter for the deactivation (range-of-motion).

Figure 9:
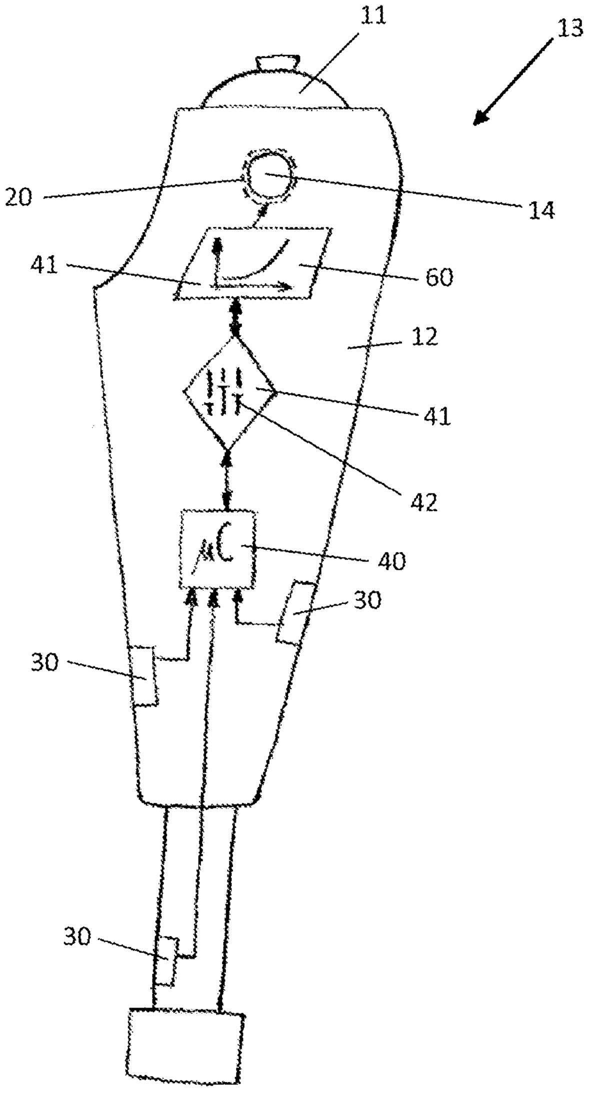
FIG. 9 shows a schematic representation of a prosthetic knee joint.

FIG. 9 shows a schematic representation of an orthopedic joint 13 in the form of a prosthetic knee joint. The prosthetic knee joint 13 has an upper part 11 and a lower part 12, which are mounted on each other so as to be rotatable about a pivot axis 14. At its distal end, the lower part 12 has connection means for fastening a prosthetic foot. A plurality of sensors 30 are likewise arranged on the lower part 12 in order to capture information and status data. For example, spatial position information, axial forces, moments, angles and/or accelerations can be measured via the sensors 30. The sensor values are transmitted to a control device 40 in which the means necessary for processing the sensor signals are present. These are, in particular, processors, storage means, software, energy stores and, if appropriate, transmitters and receivers for receiving and forwarding signals. The processed sensor signals are used to control the resistance device 20 which, in the exemplary embodiment shown, is designed as a braking device which influences a pivoting of the upper part 11 relative to the lower part 12. Also arranged on the lower part 12 is an operating element 42, which can have a control panel or on which slide controls or rotary knobs for setting parameters or threshold values of the parameters are arranged or formed. In the exemplary embodiment shown, three operating elements are shown in a display device 41 in the form of a display screen. A further display screen 41 can be arranged in the region of the pivot axis 14, and indicates the change in the threshold values. The display screen 41 is assigned an adjustment device 60, via which the resistance of the resistance device 20 can be adjusted. The display screen can also be arranged at another location on the prosthetic knee joint or the orthopedic device and can communicate wirelessly with the adjustment device 60, such that an adjustment can be made at any desired location easily accessible to the user, for example via a cell phone, a tablet or another graphical user interface.

Figure 10:
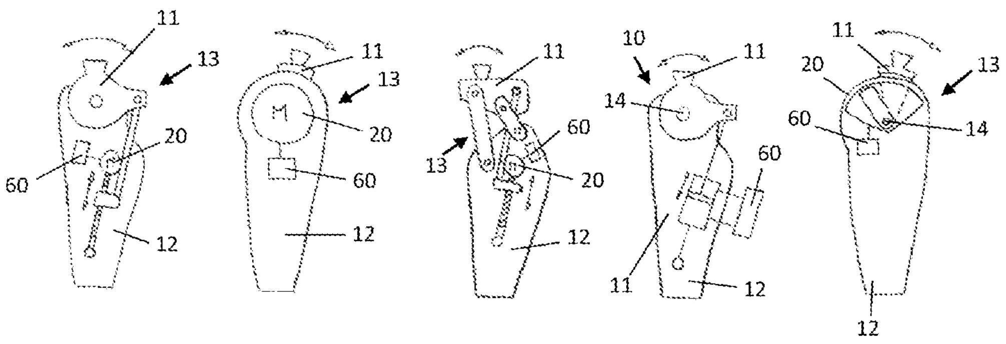
FIG. 10 shows different embodiments of resistance and adjustment devices.

In FIG. 10, five variants of adjustment devices and resistance devices are shown on the basis of prosthetic knee joints; corresponding components can also be arranged on orthoses or exoskeletons. All of the prosthetic knee joints 13 have an upper part 11 and a lower part 12. In the illustration on the left, the resistance device 20 is designed as a spindle gear mechanism, which has a motor that can be activated and deactivated via the adjustment device 60. In this way, the pivoting of the upper part 11 relative to the lower part 12 is changed and, if appropriate, locked in at least one direction.

In the second embodiment from the left, the resistance device 20 is designed as a motor which is arranged directly on the upper part 11 and is supported with respect to the lower part 12. The motor represents the resistance device 20 and can be energized differently by the adjustment device 60 via a corresponding control, such that different resistances against flexion and/or extension or locking in one of the directions can be provided.

In the middle illustration, the joint device 13 is designed as a multi-link system with four links and a non-stationary joint axis. The resistance device 20 is designed as a spindle gear mechanism with a motor which can be activated or deactivated via the adjustment device 60 in order to influence a pivoting of the upper part 11 relative to the lower part 12 or in order to effect locking.

In the fourth embodiment from the left, the resistance device 20 is designed as a hydraulic damper or pneumatic damper, which has a cylinder in which a piston with a piston rod is guided in a longitudinally displaceable manner. The piston divides the cylinder into an extension chamber and a flexion chamber, which are coupled to each other via a connecting channel. Located within the connecting channel there is at least one control valve, which is designed to be variable as regards the passage cross section. The cross section of flow can be changed via the adjustment device 60, or a fluidic connection from the extension chamber to the flexion chamber can be blocked in order thereby to influence or lock a pivotability about the pivot axis 14.

In the right-hand illustration in FIG. 10, the resistance device 20 is designed as a pivot piston system in which the pivot piston is located in a chamber and can be displaced relative to the lower part 12 in a manner corresponding to the pivoting of the upper part 11. The pivot piston likewise forms an extension chamber and a flexion chamber. A magnetorheological liquid can be located inside the pivot piston system, the viscosity of which liquid can be changed via the adjustment device 60 in the form of an activatable and deactivatable magnetic field. In this way, the flow rate from the extension chamber to the flexion chamber, and vice versa, is influenced according to the applied magnetic field and the viscosity of the medium that is thereby set.

The invention claimed is:

1. An orthopedic joint comprising an upper part and a lower part pivotably arranged on the upper part, and a resistance device which is arranged between the upper part and the lower part and which provides resistance against a pivoting movement of the upper part relative to the lower part about a pivot axis, and which has an adjustment device by means of which the resistance is adjustable, wherein the adjustment device is coupled to a control device, which is coupled to at least one sensor, such that the resistance is adjustable by means of the control device on the basis of sensor data that are transmitted from the at least one sensor to the control device, wherein the control device has stored in it a function in which the joint is locked against pivoting in at least one direction in accordance with the sensor data, and the function can be activated for locking and deactivated for unlocking on the basis of the sensor data, wherein at least one parameter for activating the function and at least one parameter for deactivating the function are correlated with one another, wherein threshold values for the parameters for activation and/or deactivation are stored, and the threshold values are variable, and wherein the threshold values for activation and deactivation are positively correlated.

2. The orthopedic joint device as claimed in claim 1, wherein a duration of a static state of the joint is stored as a parameter for activating the function.

3. The orthopedic joint device as claimed in claim 1, wherein a movement of the lower part, a movement of the upper part and/or a loading of the joint and/or rates of change of the movement and/or loading are stored as parameters for activating or deactivating the function.

4. The orthopedic joint as claimed in claim 1 wherein a spatial position of the upper part, a spatial position of the lower part and/or a connecting line between two points located proximally and distally of the pivot axis are stored as parameters for deactivating the function.

5. The orthopedic joint as claimed in claim 1 wherein the control device is connected to a display device and to an operating element for changing the parameters or the threshold values of the parameters.

6. The orthopedic joint as claimed in claim 1 wherein a gyroscope, an angle sensor, a force sensor and/or a spatial position sensor is coupled to the control device.

7. A method for controlling an orthopedic joint comprising an upper part and a lower part pivotably arranged on the upper part, and a resistance device which is arranged between the upper part and the lower part and which provides resistance against a pivoting movement of the upper part relative to the lower part about a pivot axis, and which has an adjustment device, the method comprising:

adjusting the resistance using the adjustment device on the basis of sensor data transmitted from at least one sensor to a control device connected to the adjustment device, in such a way that the joint is locked against pivoting upon activation of a function and unlocked upon deactivation of the function, wherein at least one threshold value for a parameter for activating the function and at least one threshold value for a parameter for deactivating the function are correlated with one another, and wherein the threshold values are positively correlated with one another.

8. The method as claimed in claim 7, wherein the function is activated on the basis of a duration of a static state of the joint device.

9. The method as claimed in claim 7, wherein the function is activated or deactivated on the basis of a movement of the lower part, a movement of the upper part and/or a loading of the joint.

10. The method as claimed in claim 7, wherein the function is deactivated on the basis of a spatial position of the upper part, a spatial position of the lower and/or a connecting line between two points located proximally and distally of the pivot axis.

11. The method as claimed in claim 7, wherein the threshold values for the parameters for activation and deactivation are variable.

12. A method for controlling an orthopedic joint, wherein the joint comprises an upper part and a lower part pivotably arranged on the upper part, and a resistance device which is arranged between the upper part and the lower part and which provides resistance against a pivoting movement of the upper part relative to the lower part about a pivot axis, and which has an adjustment device, the method comprising:

adjusting the resistance using the adjustment device on the basis of sensor data transmitted from at least one sensor to a control device connected to the adjustment device, in such a way that the joint is locked against pivoting upon activation of a function and unlocked upon deactivation of the function, wherein at least one threshold value for a parameter for activating the function and at least one threshold value for a parameter for deactivating the function are positively correlated with one another and are variable.

13. The method as claimed in claim 12, wherein the function is activated on the basis of a duration of a static state of the joint device.

14. The method as claimed in claim 12, wherein the function is activated or deactivated on the basis of a movement of the lower part, a movement of the upper part and/or a loading of the joint.

15. The method as claimed in claim 12, wherein the function is deactivated on the basis of a spatial position of the upper part, a spatial position of the lower part and/or a connecting line between two points located proximally and distally of the pivot axis.

* * * * *